United States Patent
Jurna et al.

(10) Patent No.: US 10,080,611 B2
(45) Date of Patent: Sep. 25, 2018

(54) SKIN TREATMENT DEVICE

(71) Applicant: KONINKLIJKE PHILIPS N.V., Eindhoven (NL)

(72) Inventors: Martin Jurna, Eindhoven (NL); Franciscus Nicolaas Kockx, Eindhoven (NL); Maria Angelina Josepha Grootel-Rensen, Eindhoven (NL); Linda Goverdina Maria Beijens, Eindhoven (NL); Antonius Maarten Nuijs, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/431,318

(22) PCT Filed: Sep. 24, 2013

(86) PCT No.: PCT/IB2013/058798
§ 371 (c)(1),
(2) Date: Mar. 26, 2015

(87) PCT Pub. No.: WO2014/057379
PCT Pub. Date: Apr. 17, 2014

(65) Prior Publication Data
US 2015/0257829 A1 Sep. 17, 2015

Related U.S. Application Data

(60) Provisional application No. 61/711,265, filed on Oct. 9, 2012.

(51) Int. Cl.
*A61B 18/20* (2006.01)
*G02B 26/12* (2006.01)
*A61B 18/00* (2006.01)

(52) U.S. Cl.
CPC ............ *A61B 18/203* (2013.01); *G02B 26/12* (2013.01); *A61B 2018/0047* (2013.01);
(Continued)

(58) Field of Classification Search
None
See application file for complete search history.

(56) References Cited

U.S. PATENT DOCUMENTS 5,371,361 A * 12/1994 Arends ................ G02B 26/12
235/462.39
5,546,214 A 8/1996 Black
(Continued)

FOREIGN PATENT DOCUMENTS

| WO | 2007095183 A2 | 8/2007 |
| WO | 2008008499 A2 | 1/2008 |
| WO | 2013036761 A1 | 3/2013 |

*Primary Examiner* — Lynsey Eiseman
*Assistant Examiner* — Qingjun Kong (57) ABSTRACT

A skin treatment device comprising a light source providing a light beam for optically treating skin, a wheel with a wheel surface for reflecting the light beam towards the skin, driving means for rotating the wheel and changing an angular position of the wheel, where different angular positions of the wheel correspond to different directions of reflection for the light beam, an angular position detector for detecting the angular position of the wheel, storage means for storing predefined skin-treatment patterns, a relation between the different angular positions of the wheel; and different reflection directions of the light beam, a control circuit coupled to the light source. The light source being controlled in dependence on the detected angular position such that, for each revolution of the wheel, the light beam is controlled to only illuminate the wheel surface in selected angular positions of the wheel to realize a predefined skin-treatment pattern.

18 Claims, 10 Drawing Sheets

(52) U.S. Cl.
CPC ........... *A61B 2018/00452* (2013.01); *A61B 2018/00779* (2013.01); *A61B 2018/2035* (2013.01); *A61B 2018/20351* (2017.05)

(56) References Cited

U.S. PATENT DOCUMENTS

| | | | | |
|---|---|---|---|---|
| 5,898,650 | A | * | 4/1999 | Porsbo .................. G11B 17/22 369/30.89 |
| 6,575,964 | B1 | | 6/2003 | Hobart |
| 6,585,725 | B1 | | 7/2003 | Mukai |
| 8,246,613 | B2 | | 8/2012 | Dover |
| 2006/0239547 | A1 | * | 10/2006 | Robinson ............. A61B 5/0059 382/162 |
| 2008/0043306 | A1 | | 2/2008 | DeBenedictis |
| 2008/0273231 | A1 | | 11/2008 | Broome |
| 2009/0195848 | A1 | * | 8/2009 | DeBenedictis ........ G02B 5/001 359/201.1 |
| 2009/0213447 | A1 | | 8/2009 | Hayashi |
| 2012/0019735 | A1 | | 1/2012 | Zuidema |
| 2012/0197357 | A1 | * | 8/2012 | Dewey ................ A61B 18/203 607/89 |
| 2012/0253331 | A1 | | 10/2012 | Liu |

\* cited by examiner

SKIN TREATMENT DEVICE

This application is the U.S. National Phase application under 35 U.S.C. § 371 of International Application No. PCT/IB2013/058798, filed on Sep. 24, 2013, which claims the benefit of U.S. Provisional Application No. 61/711,265 filed on Oct. 9, 2012. These applications are hereby incorporated by reference herein.

FIELD OF THE INVENTION

This invention relates to a skin treatment device comprising a light source for providing a light beam for optically treating a skin, a wheel with a wheel surface for reflecting the light beam towards the skin, driving means for rotating the wheel for changing an angular position of the wheel, wherein different angular positions of the wheel correspond to respective different directions of reflection for the light beam, and a control circuit for controlling the light source.

BACKGROUND OF THE INVENTION

Such a skin treatment device is, e.g., disclosed in the United States patent application published as US 2012/0197357 A1. Said skin treatment device comprises a laser source and an optical pattern generator for creating microscopic treatment zones (MTZs) of thermally denatured skin tissue surrounded by unaffected skin tissue. This treatment boosts skin repair mechanisms and improves skin appearance. An axicon wheel with a plurality of axicon segments deflects the laser beam towards a corresponding plurality of different locations on the skin surface. A control circuit controls the laser source to randomly illuminate individual axicon segments. While the user drags the device along the skin surface, a random pattern of MTZs is applied to the skin surface. An intensity level set by the user determines the density of the random pattern.

In the known device, every axicon facet has a triggering flake that is detected by a flake detector upon passing the flake detector during rotation of the axicon wheel. The flake detector is coupled to the control circuit, which determines the rotational speed of the axicon wheel, based on the flake detector signal. Based on the rotational speed of the axicon wheel and a measured speed at which the user drags the device along the skin surface, the control circuit is able to provide the randomly distributed MTZs at a more or less constant density.

Although the possibility to set an intensity level does provide some control over the operation of the device, there is still a need for improving treatment control to better adapt to differences in skin type, skin condition, skin treatment and user preferences. It may, e.g., be desirable to make the operation of the device more specific for certain skin features, such as wrinkles, fine lines or pigmented spots.

OBJECT OF THE INVENTION

It is an object of the invention to provide a skin treatment device of the kind mentioned in the opening paragraph having improved control over the provided skin treatment.

SUMMARY OF THE INVENTION

According to a first aspect of the invention, this object is achieved by providing a skin treatment device comprising a light source for providing a light beam for optically treating a skin, a wheel with a wheel surface for reflecting the light beam towards the skin, driving means for rotating the wheel for changing an angular position of the wheel, different angular positions of the wheel corresponding to respective different directions of reflection for the light beam, an angular position detector for detecting the angular position of the wheel or a parameter corresponding with said angular position, a storage means for storing a predefined skin-treatment pattern and a relation between the different angular positions of the wheel, or the parameter corresponding with said angular position, and the corresponding respective different directions of reflection for the light beam, or a parameter corresponding with said direction of reflection, and a control circuit coupled to the light source, the angular position detector and the storage means and being operative to control the light source in dependence on the angular position detected by the angular position detector in such a way that, for each revolution of the wheel, the light beam only illuminates the wheel surface in selected angular positions of the wheel to realize the predefined skin-treatment pattern.

In the skin treatment device of US 2012/0197357 A1, treatment always starts with the axicon wheel in a random and unknown position. Then the light source randomly illuminates unknown facets of the axicon wheel resulting in MTZs at random positions on the skin. For the known device, this is not really considered a problem, because for every revolution of the wheel all facets have an equal chance of being illuminated and the overall result is a homogeneous distribution of MTZs with the desired density.

With the device according to the invention it is possible to start treatment at a selected angular position of the wheel and a corresponding direction of reflection of the light beam or, generally, it is possible to provide MTZs according to a predefined pattern on the skin by successively reflecting the light beam in a selected sequence of directions of reflection corresponding with the predefined skin-treatment pattern. Because the reflection directions corresponding to the different angular positions of the wheel are fixed, knowledge of the angular position of the wheel, obtained by means of the angular position detector, makes it possible to instantaneously know the direction in which light from the light source is reflected. For example, the control circuit may control the light source to illuminate the wheel surface only during each first or second half of each revolution of the wheel. Combining the knowledge of the angular position with the stored corresponding directions of reflection makes it possible for the control circuit to create MTZs only at selected positions on the skin according to a predefined skin-treatment pattern, which may e.g. be selected by the user. While dragging the device along the skin, a skin-treatment pattern with MTZs at pre-selected locations on the skin appears instead of the random pattern generated by the known device. The skin-treatment pattern may comprise, e.g., straight vertical, horizontal or diagonal lines of MTZs. Also wobbling patterns of MTZs, or separated spots of MTZs of different shapes may be generated.

In a preferred embodiment, the angular position detector is arranged to detect a passage of an identification element associated with a predetermined one of the different angular positions of the wheel. The identification element may be a property of the wheel surface itself, an element attached to the wheel surface at a certain position or just an element provided on or at the wheel at some predetermined angular position. Of course, in addition to the first identification element also a passage of a second or even more unique identification elements may be detectable, each unique identification element corresponding to a different angular position. In general, however, the invention may be used with any kind of angular position detector for detecting the angular position of the wheel, or with any kind of detector to detect a parameter corresponding with said angular position.

In a preferred embodiment, the wheel surface comprises multiple facets for reflecting the light beam towards the skin in mutually different directions of reflection, each facet corresponding to one of the different directions of reflection. In a further embodiment, the identification element is associated with a predetermined single one of the multiple facets. An example of a suitable wheel is an axicon wheel. It is however to be noted that the invention is not at all limited to the use of faceted wheels or axicon wheels. For example, a wheel whose direction of reflection gradually changes in its circumferential direction could be used in a similar way and with similar advantageous effects. In fact, by further increasing the number of facets and decreasing the differences in orientation between subsequent facets, an approximation of such a wheel with a circumferentially gradually and continuously changing direction of reflection is obtained.

According to the invention, the storage means is operative to store a relation between the different angular positions of the wheel and the corresponding respective different directions of reflection for the light beam, or a parameter corresponding with said directions of reflection. Instead of the angular position, any parameter corresponding with said angular position may be used by the storage means. Instead of the direction of reflection, any parameter corresponding with said direction of reflection may be used by the storage means. In an exemplary embodiment, the storage means is operative to store a sequence of the multiple facets, and the control circuit is arranged to selectively illuminate the facets based on the stored sequence of the multiple facets and the passage of the predetermined single one of the multiple facets. In this embodiment, the parameter corresponding with the direction of reflection is a sequence number of the facets, and the angular position is monitored based on the passage of the predetermined single one of the multiple facets and the rotational speed of the wheel.

Optionally, the device further comprises a skin feature detector for detecting characterizing features of the skin, the feature detector being coupled to the control circuit and the control circuit being arranged to define the predefined skin-treatment pattern, based on the detected characterizing features. The detected skin features may, e.g., be wrinkles, pigment spots or skin lesions. The applied treatment pattern may then, e.g., follow the wrinkle or treat the pigment spot without also treating the surrounding skin areas. Exemplary detectors for detecting skin features and skin properties are described in, e.g., United States patent application US 2006/0239547 A1.

The detection of the passage of the predetermined single one of the multiple facets may be performed in many different ways. The reliability of the detection of said passage may be improved by combining two different ways of recognizing a specific facet. For example, the predetermined single one of the multiple facets may have a translucency coefficient different from that of the other facets, and the angular position detector may comprise a light sensor for detecting a portion of the light beam having passed through the predetermined single one of the multiple facets.

Alternatively, each facet may comprise a flake, the flake of the predetermined single one of the multiple facets being geometrically different from the flakes of the other facets, the angular position detector being arranged to detect the geometrically different flake. In this embodiment, the regular trigger signal for triggering the light source can also be used for detecting the passage of the predetermined single one of the multiple facets. All facets, except the predetermined single one of the multiple facets, may provide the same trigger signal as known from the prior art. Each time the predetermined single one of the multiple facets passes, i.e. once per revolution of the wheel, the angular position detector provides a distinct signal that is recognized by the control circuit. Geometrically different may, e.g., mean that the geometrically different flake is shorter than the other flakes or that the geometrically different flake comprises two flake parts separated by a gap.

Alternatively, the wheel surface may comprise a hole which is associated with the predetermined single one of the multiple facets, and wherein the angular position detector comprises a second light source and a light sensor arranged such that light from the second light source can reach the light sensor through the hole. In a similar way, a further reflective surface may be provided at the wheel surface, wherein the further reflective surface is associated with the predetermined single one of the multiple facets, and wherein the angular position detector comprises a second light source and a light sensor, arranged such that light from the second light source can reach the light sensor via the further reflective surface.

These and other aspects of the invention are apparent from and will be elucidated with reference to the embodiments described hereinafter.

DETAILED DESCRIPTION OF THE INVENTION

Figure 1:
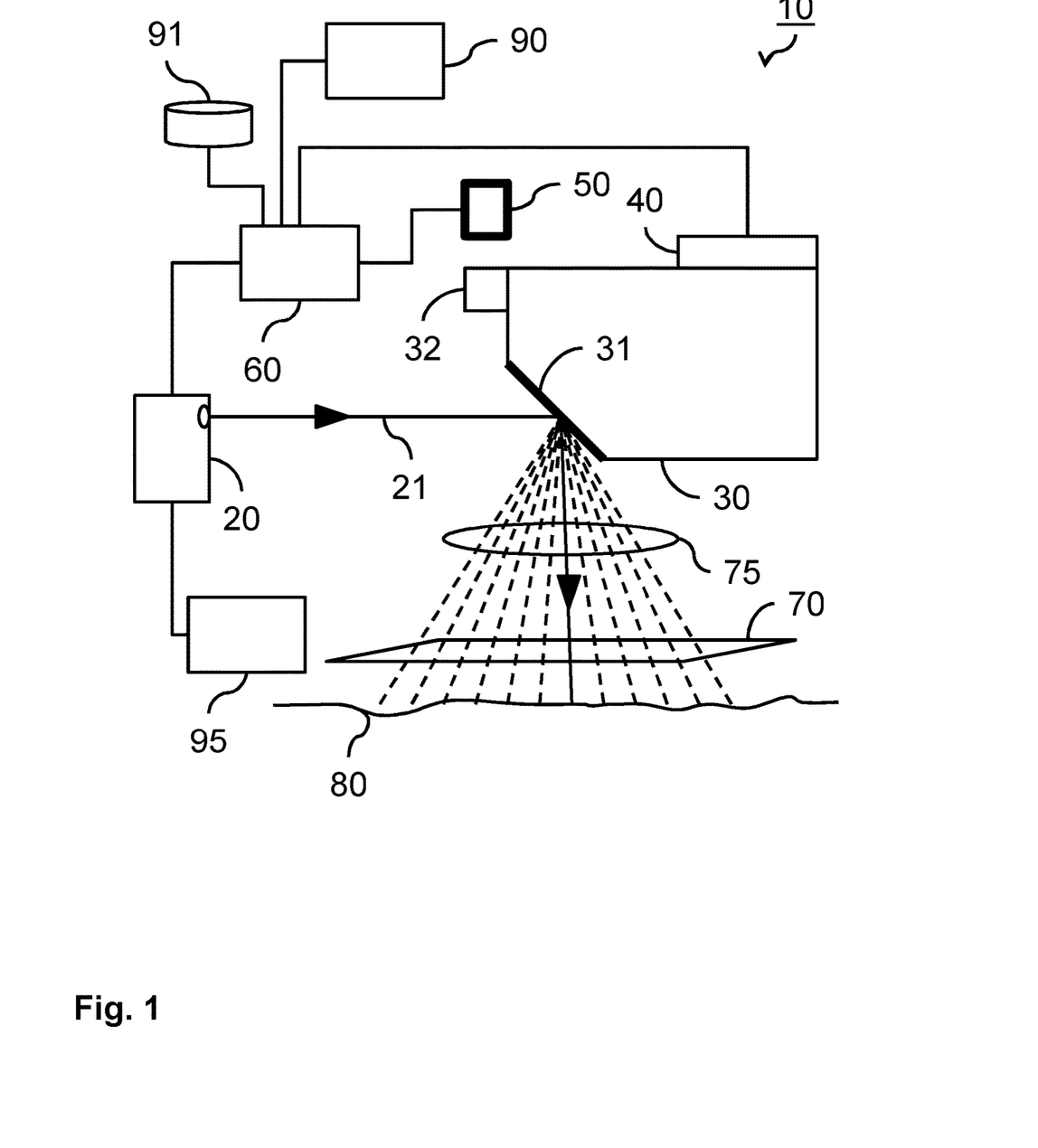
FIG. 1 schematically shows a skin treatment device.

FIG. 1 schematically shows a skin treatment device 10. The device 10 comprises a light source 20, in this event a laser source 20, for providing a light beam 21. An axicon wheel 30 with a plurality of axicon facets 31 deflects the light beam 21 through an objective lens 75 and an exit window 70 of the device 10 towards a skin 80. Each axicon facet 31 provides a respective different direction of reflection for the light beam 21. Accordingly, during rotation of the axicon wheel 30, the light beam 21 is reflected towards a corresponding plurality of different locations at the skin 80. At the skin 80, the light beams create microscopic treatment zones (MTZs) of thermally denatured skin tissue surrounded by unaffected tissue. This treatment boosts skin repair mechanisms and improves skin appearance. The laser source 20 is coupled to a control circuit 60 which controls the laser source to illuminate individual axicon facets 31 at selected moments. The axicon wheel 30 is rotated by driving means 40, such that the different facets 31 of the wheel 30 successively pass the path of the incoming light beam 21. The reflective surface areas of the different facets 31 of the wheel 30 are oriented at different angles in order to reflect the light 21 into different directions, causing the light to impinge on the skin 80 at different positions within a range of reachable positions.

The axicon wheel 30 further comprises triggering flakes 32 which are provided next to the facets 31. Passage of the triggering flakes 32 is detected by a flake detector 50. The flake detector 50 is coupled to the control circuit 60. The frequency of the trigger signal generated by the flake detector 50 is dependent on the rotational speed of the axicon wheel 30. Based on the trigger signal, the control circuit 60 controls the light source 20 to emit light during a desired portion of each rotation of the wheel 30. In a prior art example of an axicon wheel 30 with twelve facets 31, the control circuit 60 may, e.g., provide a light pulse at 2, 4, 6 or even 12 of the facets 31 passing during one rotation. Furthermore, the device 10 may comprise means 90 for determining the hand speed with which the user drags the device 10 along the skin surface 80. The control circuit 60 is able to adapt a firing rate of the light source 20 depending on the measured hand speed in order to provide the MTZs at a more or less constant density which is independent of the hand speed.

According to the invention, the control circuit 60 of the device 10 is not only capable of adapting the firing rate of the light source 20 to a rotational speed of the axicon wheel 30 and the measured hand speed of the user, but the control circuit 60 is also arranged to select the actual facets 31 that are to be illuminated by the light source 20 to provide a predefined skin-treatment pattern of MTZs at the skin 80. Below, with reference to FIGS. 5 to 9, it is explained how this is achieved. The desired skin-treatment pattern may for example be selected by the user.

The device 10 may further comprise a skin feature detector 95 for detecting, e.g., wrinkles, skin lesions, pigmented spots or other skin features. The skin feature detector 95 may also be operative to detect skin properties such as color or skin moisture. The skin feature detector may, e.g., comprise a camera for observing the skin 80 or a detector for detecting and analyzing the treatment light beam 21 after reflecting at the skin surface 80. The skin feature detector is coupled to the control circuit 60, such that the treatment can be adapted to the detected features. For example, the light source 20 may be controlled such that the treatment only affects a detected wrinkle or pigmented spot. The light source 20 may also be controlled such that selected parts of the skin are not treated.

Figure 2:
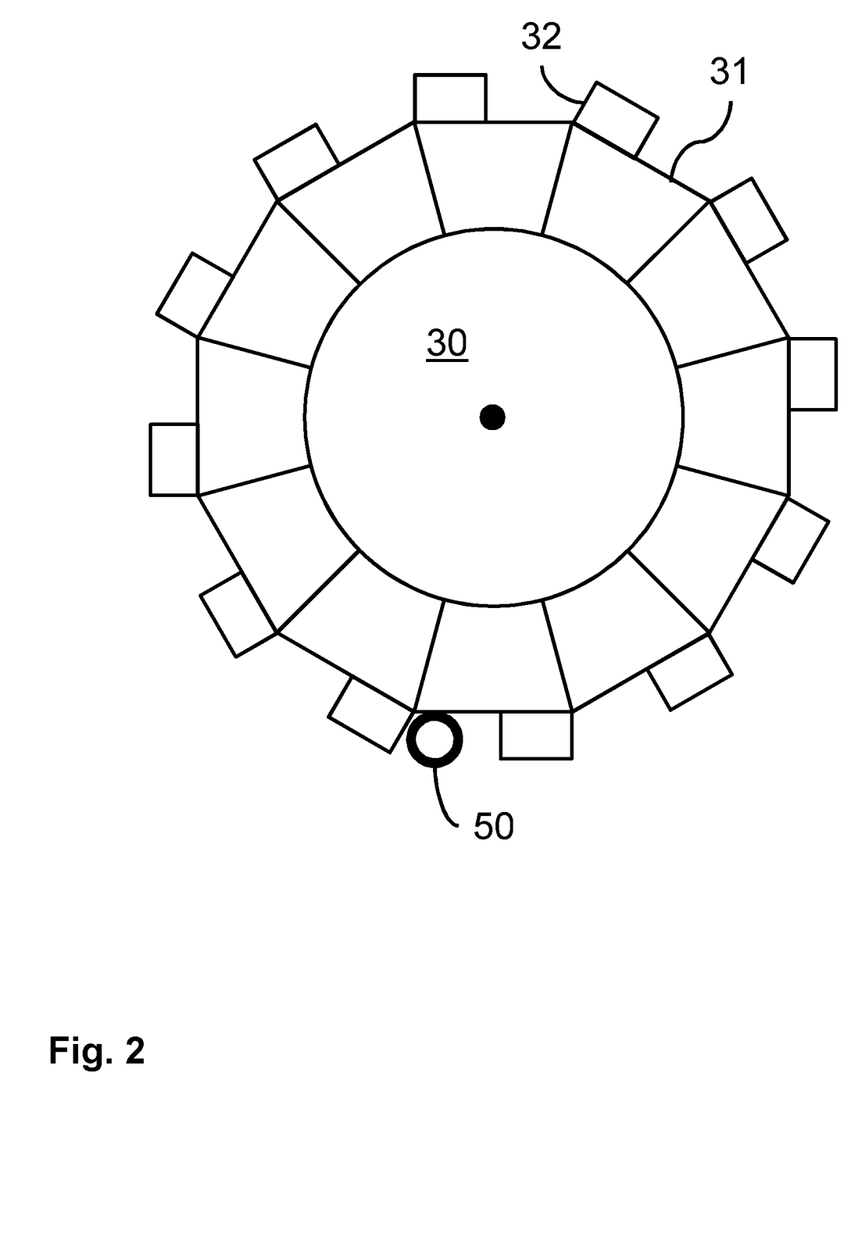
FIG. 2 schematically shows a top view of an axicon wheel for a skin treatment device.
Figure 3:
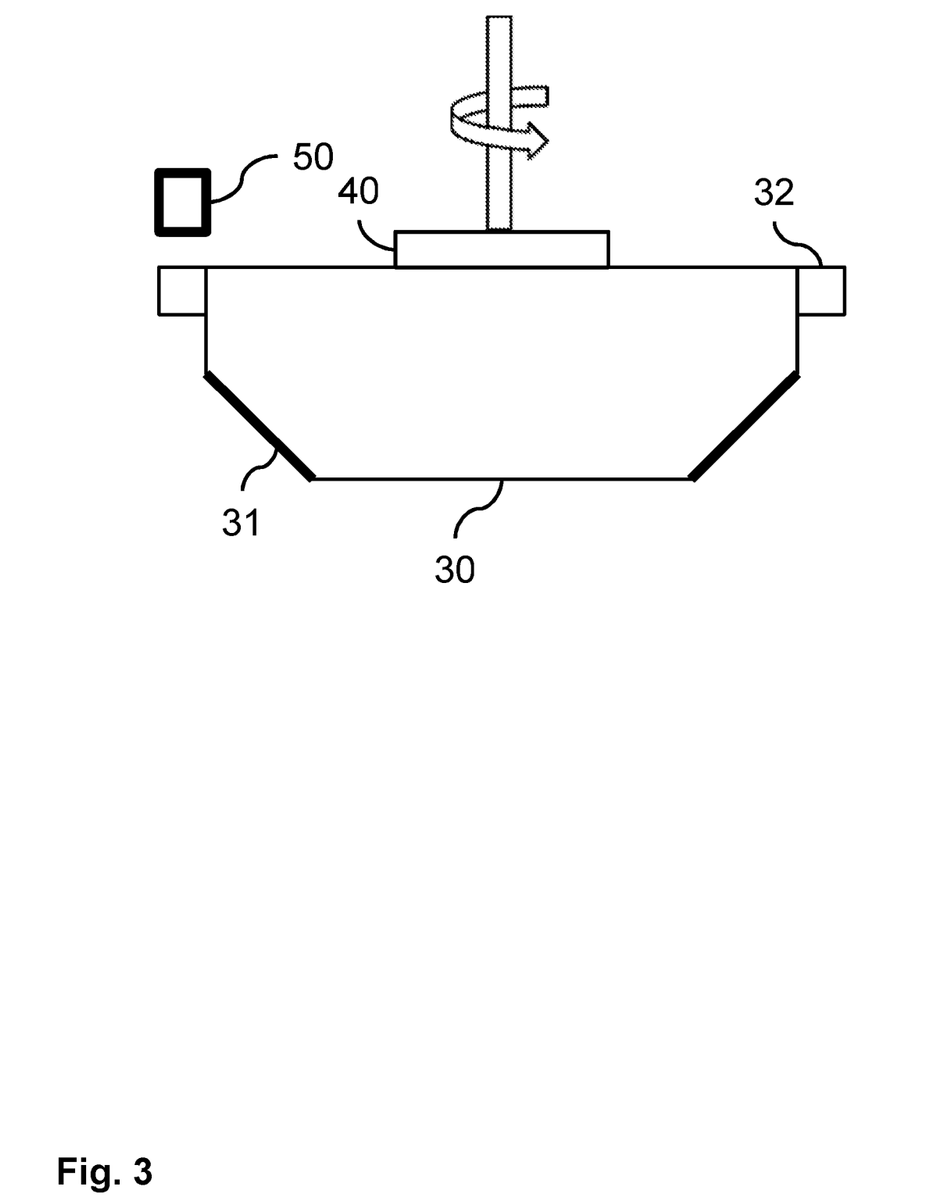
FIG. 3 shows a cross section of the axicon wheel of FIG. 2, FIGS. 4a, 4b and 4c show examples of skin-treatment patterns.

FIG. 2 schematically shows a top view of a prior art axicon wheel 30 for the skin treatment device 10 of FIG. 1. The axicon wheel 30 comprises twelve facets 31 for redirecting and reflecting light coming from the light source 20. Each facet 31 is accompanied by a trigger flake 32. Passage of the trigger flakes 32 is detected by the flake detector 50. The light source 20 is controlled in dependence on the trigger signal generated by the flake detector 50. FIG. 3 shows a cross section of the axicon wheel 30 of FIG. 1.

Figure 4A:
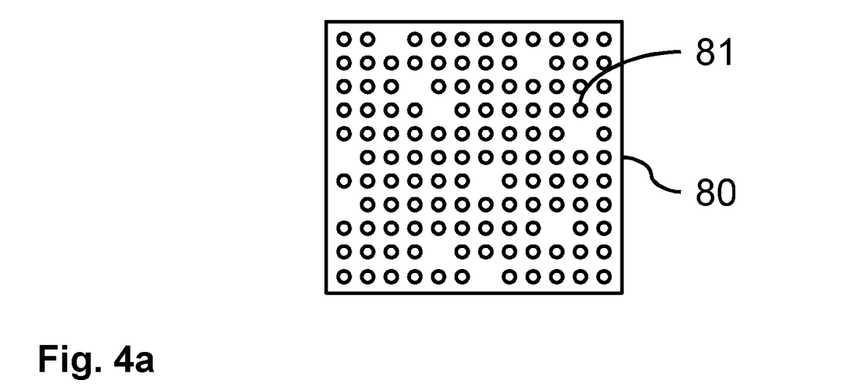
Figure 4B:
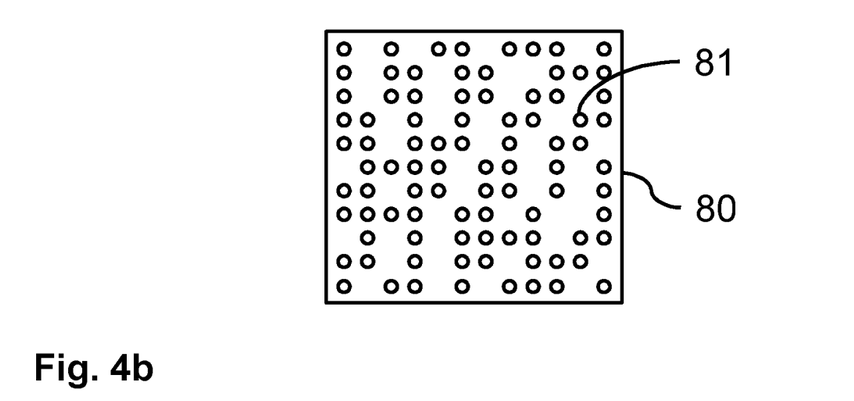
Figure 4C:
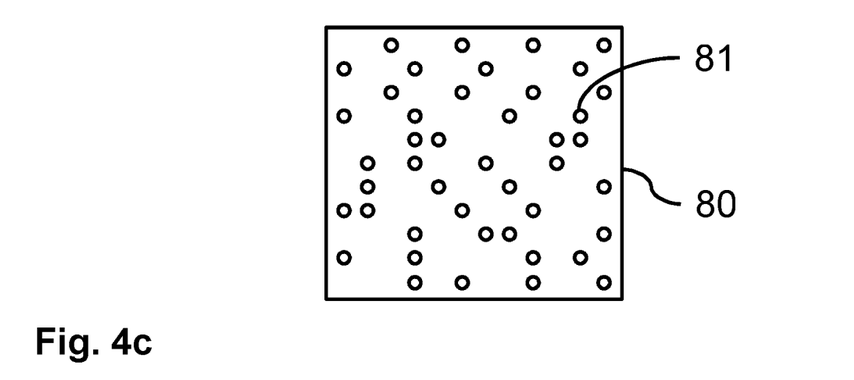

FIGS. 4a, 4b and 4c show examples of treatment patterns that may be obtained with the skin treatment device of FIG. 1 when the prior art axicon wheel 30 according to FIG. 2 is used. These exemplary patterns of MTZs 81 on the skin 80 are obtained by randomly illuminating facets 31 on the axicon wheel 30 at a controlled firing rate while dragging the device 10 over the skin surface 80. The firing rate is controlled in dependence on the observed rotational speed of the axicon wheel and the measured hand speed of the user. The firing rate is controlled such that a more or less constant density of MTZs is provided independent of the hand speed. The density may be selected, e.g., dependent on a user-selected intensity level and/or on one or more automatically detected skin properties. In these FIGURES, FIG. 4a shows an example of a high-density pattern, FIG. 4b shows an example of a medium-density pattern and FIG. 4c shows an example of a low-density pattern.

Figure 5A:
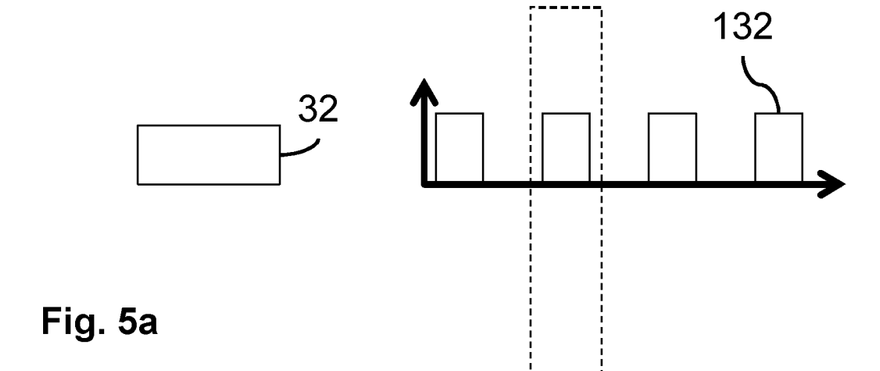
FIGS. 5a, 5b and 5c show exemplary trigger signals.

In FIG. 5a, a 'normal' trigger flake 32 is shown together with the resulting trigger signal 132 generated by the flake detector 50. In this example, all flakes 32 of the prior art axicon wheel 30 have the same shape (at least in the dimensions observed by the flake detector 50). The frequency of the trigger signal 32 depends on the rotational speed of the wheel 30. The width of the trigger pulses depends on the width of the trigger flakes 32.

Figure 5B:
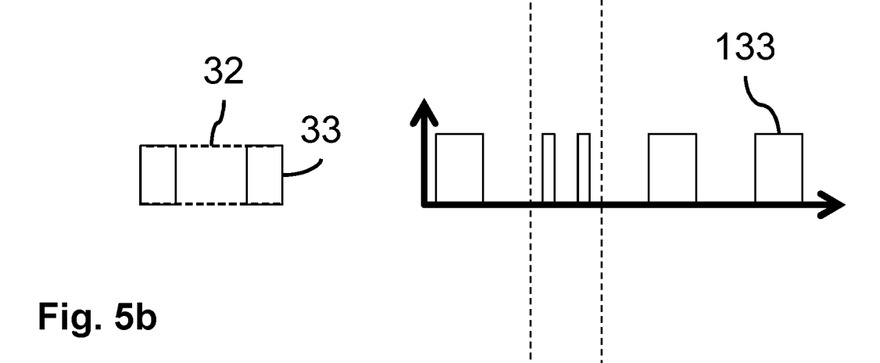
Figure 5C:
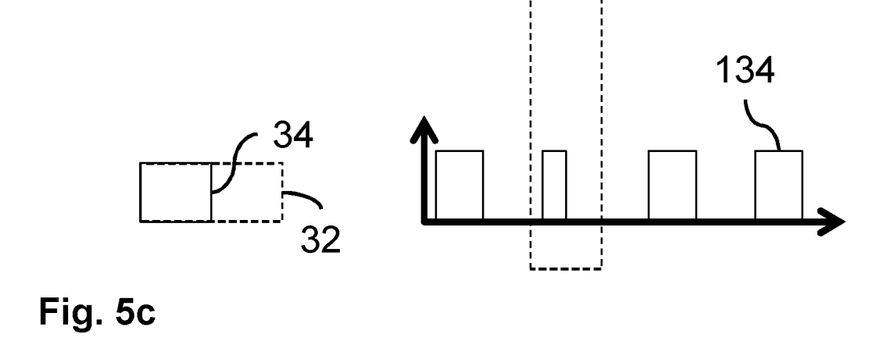

FIGS. 5b and 5c show exemplary trigger signals for devices 10 according to the invention having an axicon wheel 30 with mutually different trigger flakes 33, 34. In FIG. 5b, at least one of the trigger flakes 33 is made different from the others. In this example, the flake 33 is made different by splitting one normal flake 32 into two parts with a gap in between. Every time this aberrant flake 33 passes the flake detector 50, the trigger signal 133 is different from the trigger signal 132 when the normal flakes 32 pass. Instead of one trigger pulse, the aberrant flake 33 causes two distinct smaller pulses. When this aberrant flake 33 is detected, the control circuit knows that the facet 31 associated with this aberrant flake 33 passes the detector and thus also knows the exact rotational position of the axicon wheel 30. This makes it possible for the control circuit 60 to enable only selected facets 31 of the axicon wheel 30 to be illuminated.

FIG. 5c shows an alternative way of providing an aberrant flake 34. This flake 34 is half as wide as a normal flake 32, resulting in a smaller trigger pulse in the trigger signal 134. Detection of this smaller pulse indicates passage of the predetermined facet 34 associated with the aberrant flake 34.

FIGS. 6a, 6b, 6c, 7a, 7b and 7c show examples of skin-treatment patterns obtained by a skin treatment device according to the invention. The patterns of MTZs 81 at the skin 80 are provided by selectively illuminating some or all of the facets 31 at the wheel 30, one scan line at a time. It is to be noted that the patterns shown in these figures (and in FIGS. 4a, 4b, 4c) show a horizontal scan line and a device 10 that moves over the skin surface 80 in a direction perpendicular to the scan line. When the device is dragged along the skin surface in a different, possibly not straight, direction, then the pattern will be skewed accordingly. Optionally, the selection of facets 31 to be illuminated may depend on the direction of movement of the device.

Figure 6A:
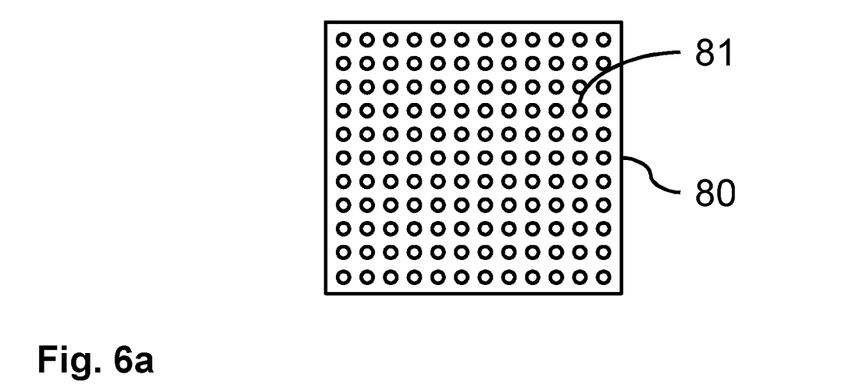
FIGS. 6a, 6b, 6c, 7a, 7b and 7c show examples of skin-treatment patterns obtained by a skin treatment device according to the invention.

In FIG. 6a, a pattern is shown that is obtained by illuminating, at every scan line, all facets 31 of the axicon wheel 30. For obtaining this pattern, it is not necessary for the device 10 to be able to know the exact angular position of the wheel 30. For the patterns of FIGS. 6b and 6c (and 7a, 7b, 7c), it is important to determine the angular position of the wheel, for example by detecting when a predetermined single one of the multiple facets passes a selected position in the device 10. When detecting the passage of the predetermined single one of the multiple facets, the exact sequence of different facet orientations can be determined, which allows drawing the desired MTZ patterns on the skin 80. The device may however use any suitable angular position detector for detecting the actual angular position of the wheel 30.

Figure 6B:
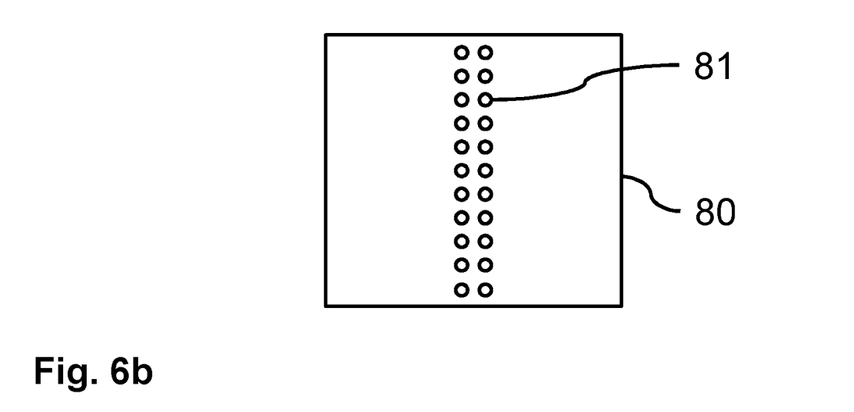
Figure 6C:
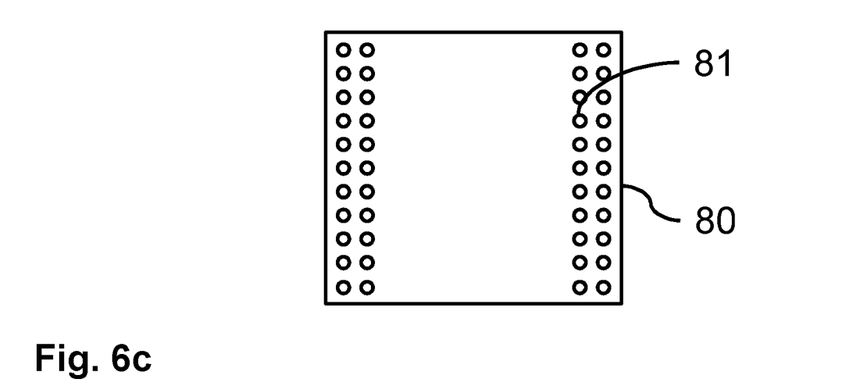

FIG. 6b shows a pattern obtained by reflecting the light beam at only two of the facets 31. These two facets may or may not be provided adjacent to each other on the axicon wheel 30. The orientation of these two facets 31 is only slightly different, resulting in the corresponding MTZs 81 being located adjacent to each other. The small vertical treatment pattern may follow a wrinkle or other skin feature that is detected by a skin feature detector of the device 10. FIG. 6c shows a pattern requiring four facets 31 to be illuminated for every scan line. For both the patterns of FIGS. 6b and 6c, the same facets 31 are illuminated at every scan line (assuming that no corrections are made for any displacements of the device 10 in directions parallel to the orientation of the scan line).

It is to be noted that for a pattern of, e.g., a single vertical line it is not necessary for the control circuit 60 to know the exact orientations and sequence of orientations of all the facets 31 on the wheel 30. In that situation, it would be sufficient to detect the passage of a predetermined single one of the facets and to illuminate the same facets at each rotation of the wheel 30.

Figure 7A:
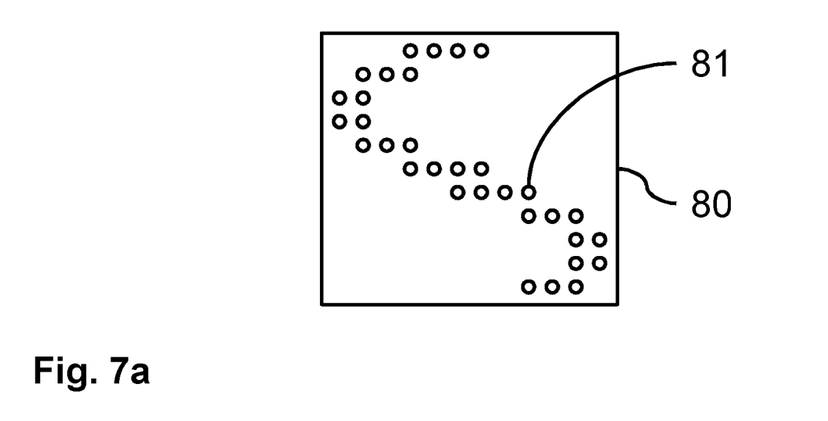
Figure 7B:
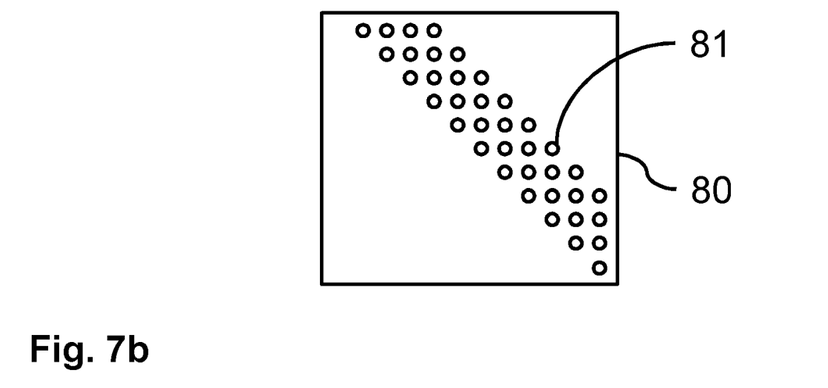
Figure 7C:
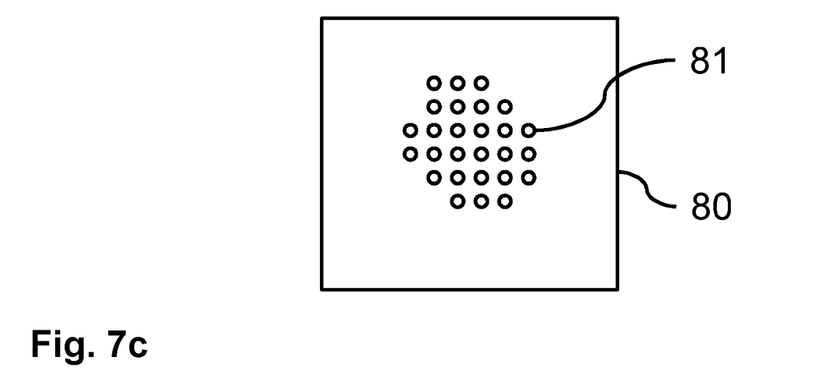

For the patterns of FIGS. 7a, 7b and 7c, different facets 31 are selected at each scan line. For obtaining these patterns, knowledge of the positions and orientations of all facets is required. A storage means 91 is coupled to the control circuit and stores the predefined skin-treatment pattern and a relation between the different angular positions of the wheel 30 and the corresponding respective different directions of reflection for the light beam 21. For example, the storage means 91 may store a database comprising a list of facet numbers, their positions at the wheel 30 and the corresponding directions of reflection. In addition, the database may store information about which facet is associated with which identification element. The control circuit 60 is operative to control the light source 20 in dependence on the angular position detected by the angular position detector, in this example the passage of the identification element, in such a way that, for each revolution of the wheel 30, the light beam 21 only illuminates the wheel surface at selected angular positions or facets to realize the predefined skin-treatment pattern. Like the patterns of FIGS. 6b and 6c, the patterns of FIGS. 7a, 7b and 7c may follow specific detected skin features or may just be selected and applied at the position where the device happens to be placed at the skin surface 80.

Figure 8:
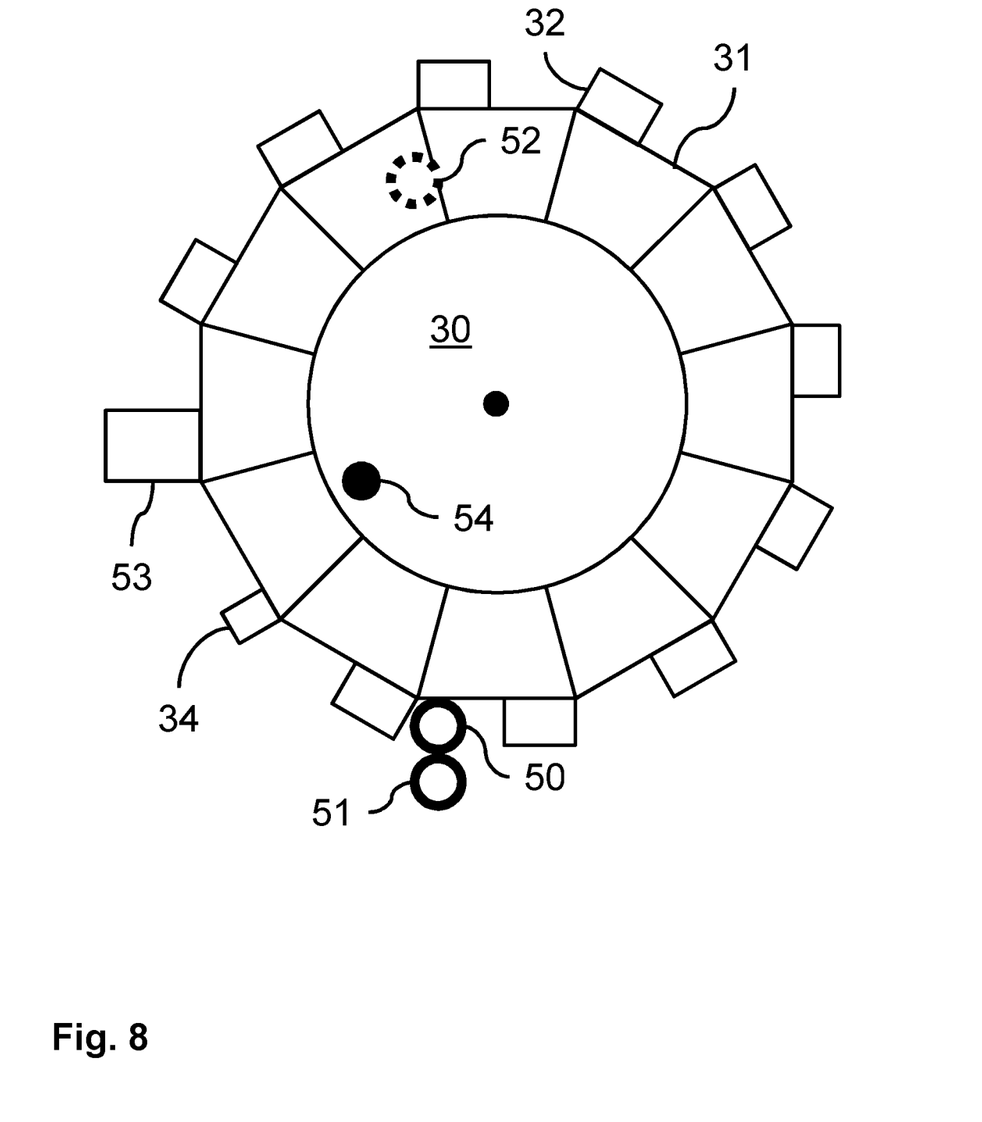
FIG. 8 shows some examples of angular position detectors of a skin treatment device according to the invention.

FIG. 8 shows some examples of angular position detectors in a skin treatment device according to the invention. First of all, the normal flake detector 50 that has already been described above may be used for detecting a flake 34 with a different shape. The flake detector 50 may, e.g., be able to detect the shorter flake 34 that has also been discussed above with reference to FIG. 5c. Alternatively, an additional flake detector 51 may be provided adjacent to the first flake detector 50 for detecting a longer flake 53 that only passes once for every revolution of the wheel 30. A similar effect is obtained by providing one shorter flake, such that the additional flake detector 51 detects all flakes except the shorter one. The predetermined facet 31 then is the facet 31 for which only the first flake detector 50 provides a trigger pulse.

Another way of detecting specific facets 31 is to place a photo detector 52 behind the facets 31 of the axicon wheel 30 and make the predetermined single one of the facets slightly more or slightly less translucent than the other ones. When the different facet passes the photo detector 52, the photo detector signal provides a different signal which thus indicates the passage of the predetermined single one of the facets. If the light source 20 is controlled such that all facets are illuminated, then the treatment light beam 21 may also be used for detecting the different facets. Otherwise, it may be preferred to use a separate additional light source for this purpose.

As a further alternative, the wheel surface may comprise a special marking 54 that is detected by a detector (not shown) capable of recognizing the marking. For example, the marking 54 is a colored dot detected by a camera or a reflective spot detected by a combination of a light emitter and a photo detector. The marking 54 may also be a hole in the wheel 30, with a light emitter and a photo detector being provided on opposite sides of the wheel 30.

Figure 9:
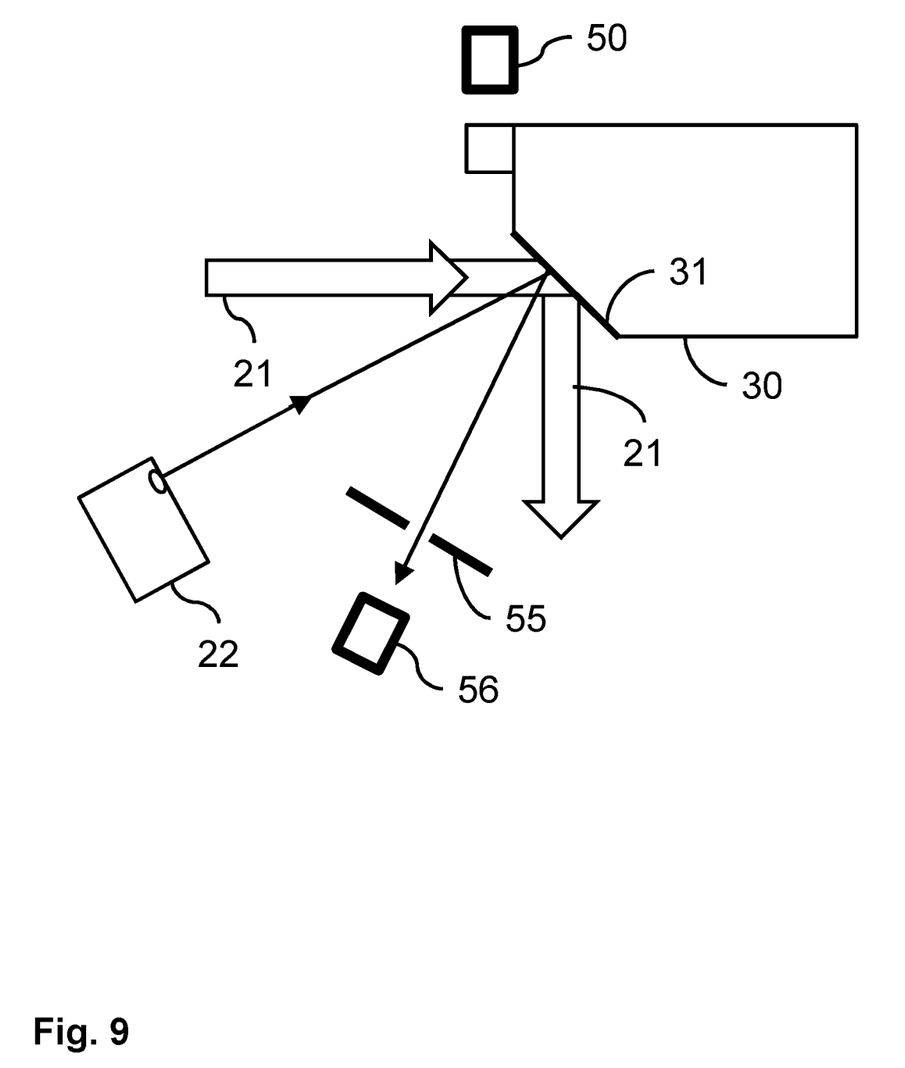
FIG. 9 shows a further example of an angular position detector of a skin treatment device according to the invention.

FIG. 9 shows a further example of an angular position detector in a skin treatment device according to the invention. This embodiment makes use of the differences in orientation between the different facets 31. Here, an additional light source 22 is provided and a photo detector 56 for detecting light from the additional light source 22 after reflection at the predetermined facet 31. Different facets 31 reflect the light in different directions. A small slit 55 in front of the photo detector 56 ensures that only light reflected at precisely the correct angle by the predetermined single one of the multiple facets reaches the photo detector 56. Light that is reflected by facets other than the predetermined single one of the facets will not reach the photo detector 56. The photo detector 56 thus provides a trigger signal every time the predetermined single one of the multiple facets 31 passes.

Figure 10:
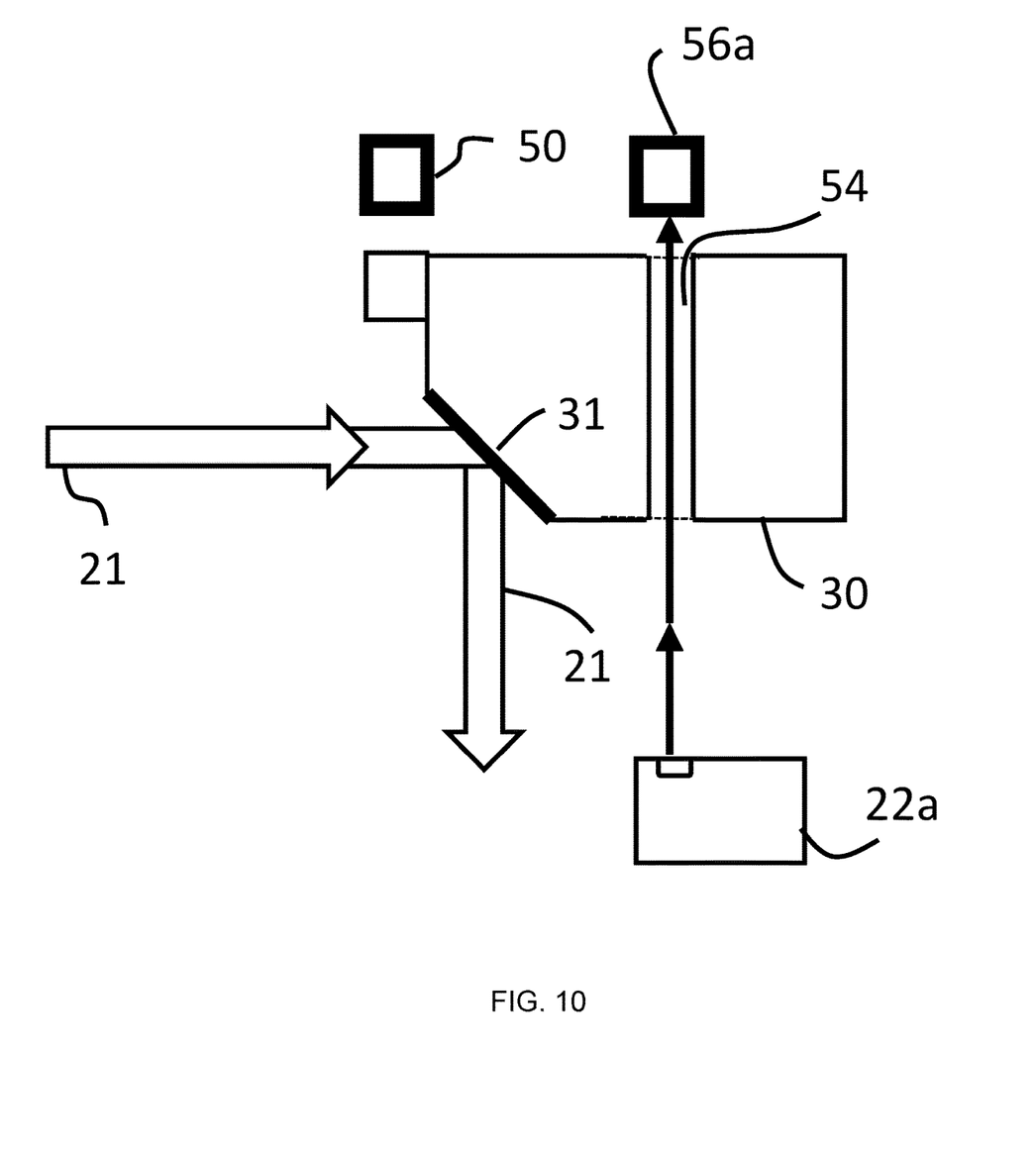
FIG. 10 shows a further example of an angular position detector of a skin treatment device according to the invention.

FIG. 10 shows a further example of an angular position detector in a skin treatment device according to the invention. This embodiment makes use of a hole 54 in the wheel surface which is associated with a predetermined single one of the multiple facets. Here, an additional light source 22a is provided and a photo detector 56 for detecting light from the additional light source 22. The additional light source 22a and light sensor 56a are arranged such that light from the additional light source 22a can reach the light sensor 56a through the hole.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A skin treatment device comprising:
a light source configured to provide a light beam for optically treating a skin,
a wheel with a wheel surface for reflecting the light beam towards the skin, the wheel surface comprising multiple facets for reflecting the light beam towards the skin in a mutually different direction of reflection, each facet associated with a different predetermined angular position in the wheel, each facet corresponding to one of the different directions of reflection,
a single identification element associated with a predetermined single one of the multiple facets, wherein the single identification element comprises a unique element attached to the wheel surface at a single predetermined angular position,
driving means configured to rotate the wheel for changing an angular position of the wheel, different angular positions of the wheel corresponding to respective different directions of reflection for the light beam,
an angular position detector arranged to detect a passage of the single identification element associated with a predetermined one of the different angular positions of the wheel, the angular position detector including a light sensor,
a storage means configured to store a predefined skin-treatment pattern and a relation between the different angular positions of the wheel and the corresponding respective different directions of reflection for the light beam, or a parameter corresponding with said direction of reflection,
a control circuit coupled to the light source, the angular position detector and the storage means,
the control circuit being configured to:
start treatment at a predetermined angular position of the wheel and a corresponding direction of reflection of the light beam,
create microscopic treatment zones at selected positions on the skin,
recognize a distinct signal that is provided by the angular position detector that is generated each time the single identification element passes once per revolution of the wheel,
selectively illuminate the facets based on a passage of a stored sequence of selected facets to be illuminated from among the multiple facets to provide a predefined skin-treatment pattern of microscopic treatment zones at the skin,
control the light source in dependence on the angular position detected by the angular position detector, such that, for each revolution of the wheel, the light beam only illuminates the wheel surface in selected angular positions of the wheel to realize the predefined skin-treatment pattern,
a skin feature detector configured to detect characterizing features of the skin, the skin feature detector being coupled to the control circuit and the control circuit being arranged to adapt a predefined skin-treatment pattern based on the detected characterizing features.

2. A skin treatment device as claimed in claim 1, wherein the storage means is operative to store a sequence of the multiple facets, and wherein the control circuit is arranged to selectively illuminate the facets, based on the stored sequence of the multiple facets and the passage of the predetermined single one of the multiple facets.

3. A skin treatment device as claimed in claim 1, wherein the characterizing features are wrinkles, pigment spots or skin lesions.

4. A skin treatment device as claimed in claim 1, wherein the angular position detector is arranged to detect a passage of a second predetermined one of the multiple facets.

5. A skin treatment device as claimed in claim 1, wherein the physical property of the wheel surface is a translucency coefficient.

6. A skin treatment device as claimed in claim 1, wherein the geometrically different flake is shorter than the other flakes.

7. A skin treatment device as claimed in claim 1, wherein the geometrically different flake comprises two flake parts separated by a gap.

8. A skin treatment device as claimed in claim 1, wherein the wheel surface comprises a hole which is associated with the predetermined single one of the multiple facets, and wherein the angular position detector comprises a second light source and a light sensor arranged such that light from the second light source can reach the light sensor through the hole.

9. A skin treatment device as claimed in claim 1, wherein the wheel surface comprises a further reflective surface which is associated with the predetermined single one of the multiple facets, and wherein the angular position detector comprises a second light source and a light sensor, arranged such that light from the second light source can reach the light sensor via the further reflective surface.

10. A skin treatment device as claimed in claim 1, wherein the angular position detector is configured to detect a parameter corresponding with said angular position.

11. A skin treatment device as claimed in claim 1, wherein the storage means is further configured to store a parameter corresponding with said angular position.

12. A skin treatment device as claimed in claim 1, wherein the storage means is further configured to store a parameter corresponding with said direction of reflection.

13. A skin treatment device as claimed in claim 1, wherein the characterizing features of the skin comprise at least one of: wrinkles, pigment spots and skin lesions.

14. A skin treatment device as claimed in claim 1, wherein the characterizing features of the skin comprise at least one of: skin color and skin moisture.

15. A skin treatment device as claimed in claim 1, wherein said control circuit is adapted to only affect a detected wrinkle or pigmented spot.

16. A skin treatment device as claimed in claim 1, wherein said control circuit is adapted to be controlled in a manner such that selected parts of the skin are not treated.

17. A skin treatment device as claimed in claim 1, wherein said single identification element associated with said predetermined single one of the multiple facets is a physical property of the wheel surface.

18. A skin treatment device comprising:
a light source configured to provide a light beam for optically treating a skin,
a wheel with a wheel surface for reflecting the light beam towards the skin, the wheel surface comprising multiple facets for reflecting the light beam towards the skin in a mutually different direction of reflection, each facet associated with a different predetermined angular position in the wheel, each facet corresponding to one of the different directions of reflection, each facet comprising a corresponding flake, wherein a flake of a predetermined single one of the multiple facets is geometrically different from the flakes of the other facets to provide a different triggering pulse from the other flakes at a predetermined angle position, driving means configured to rotate the wheel for changing an angular position of the wheel, different angular positions of the wheel corresponding to respective different directions of reflection for the light beam, an angular position detector arranged to detect a passage of the geometrically different flake at said predetermined angle position, the angular position detector including a light sensor, a storage means configured to store a predefined skin-treatment pattern and a relation between the different angular positions of the wheel and the corresponding respective different directions of reflection for the light beam, or a parameter corresponding with said direction of reflection, a control circuit coupled to the light source, the angular position detector and the storage means, the control circuit being configured to:
   start treatment at a predetermined angular position of the wheel and a corresponding direction of reflection of the light beam,
   create microscopic treatment zones at selected positions on the skin,
   recognize a distinct signal that is provided by the angular position detector that is generated each time the geometrically different flake passes once per revolution of the wheel,
   selectively illuminate the facets based on a passage of a stored sequence of selected facets to be illuminated from among the multiple facets to provide a predefined skin-treatment pattern of microscopic treatment zones at the skin,
   control the light source in dependence on the angular position detected by the angular position detector, such that, for each revolution of the wheel, the light beam only illuminates the wheel surface in selected angular positions of the wheel to realize the predefined skin-treatment pattern, a skin feature detector configured to detect characterizing features of the skin, the skin feature detector being coupled to the control circuit and the control circuit being arranged to adapt a predefined skin-treatment pattern based on the detected characterizing features.

* * * * *